(12) United States Patent
Perouse

(10) Patent No.: US 10,772,726 B2
(45) Date of Patent: Sep. 15, 2020

(54) BIOLOGICAL VALVE TREATMENT DEVICE WITH PUSHING MEMBER OF THE VALVE

(71) Applicant: LABORATOIRES INVALV, Dury (FR)

(72) Inventor: Eric Perouse, Paris (FR)

(73) Assignee: LABORATORIES INVALV, Dury (FR)

( * ) Notice: Subject to any disclaimer, the term of this patent is extended or adjusted under 35 U.S.C. 154(b) by 199 days.

(21) Appl. No.: 15/810,805

(22) Filed: Nov. 13, 2017

(65) Prior Publication Data

US 2018/0132999 A1  May 17, 2018

(30) Foreign Application Priority Data

Nov. 14, 2016 (FR) ...................................... 16 60976

(51) Int. Cl.
*A61F 2/24* (2006.01)
*A61M 25/10* (2013.01)
(Continued)

(52) U.S. Cl.
CPC ............ *A61F 2/243* (2013.01); *A61F 2/2409* (2013.01); *A61F 2/2433* (2013.01); *A61F 2/2436* (2013.01); *A61B 17/00234* (2013.01); *A61B 17/3468* (2013.01); *A61B 2017/00247* (2013.01); *A61F 2/2418* (2013.01);
(Continued)

(58) Field of Classification Search
CPC ...... A61F 2/243; A61F 2/2409; A61F 2/2436; A61F 2/2418; A61F 2/2439; A61F 2/2466; A61F 2/2433; A61F 2/2427
See application file for complete search history.

(56) References Cited

U.S. PATENT DOCUMENTS

2011/0144742 A1* 6/2011 Madrid ................. A61F 2/2433
623/2.11
2013/0035759 A1* 2/2013 Gross .................... A61F 2/2439
623/2.38
(Continued)

FOREIGN PATENT DOCUMENTS

FR 2945440 11/2010
FR 3002084 8/2014

OTHER PUBLICATIONS

Preliminary Search Report for FR 1660976, dated Feb. 27, 2017.

*Primary Examiner* — Katrina M Stransky
(74) *Attorney, Agent, or Firm* — B. Aaron Schulman, Esq.; Stites & Harbison, PLLC

(57) ABSTRACT

This treatment device (10) for a biological valve includes:
an implant (12) having a proximal sleeve (14), deployable between a retracted configuration and a deployed configuration, and comprising a plurality of proximal arms (32) intended to bear on a first face of a leaflet (18) or on an annulus (17) of the valve,
a release tool (14) for releasing the implant (12), the implant (12) being mounted in the release tool (14) in its retracted configuration.
The device (10) comprises a pushing member (16) for pushing the face of the valve leaflet (18) away from a free end of the proximal arms (32), movable relative to the implant (12) kept in its configuration retracted in the release tool (14) between a withdrawn position and a deployed position pushing the face of the leaflet (18).

20 Claims, 12 Drawing Sheets

(51) Int. Cl.
  *A61B 17/34* (2006.01)
  *A61B 17/00* (2006.01)

(52) U.S. Cl.
  CPC .. *A61F 2210/0014* (2013.01); *A61M 25/1011* (2013.01); *A61M 2025/1015* (2013.01); *A61M 2025/1079* (2013.01)

(56) References Cited

U.S. PATENT DOCUMENTS

| | | | |
|---|---|---|---|
| 2014/0249622 A1* | 9/2014 | Carmi | A61F 2/2442 623/2.11 |
| 2015/0265442 A1 | 9/2015 | Styrc | |
| 2016/0095700 A1 | 4/2016 | Righini | |
| 2016/0302922 A1* | 10/2016 | Keidar | A61F 2/2433 |

* cited by examiner

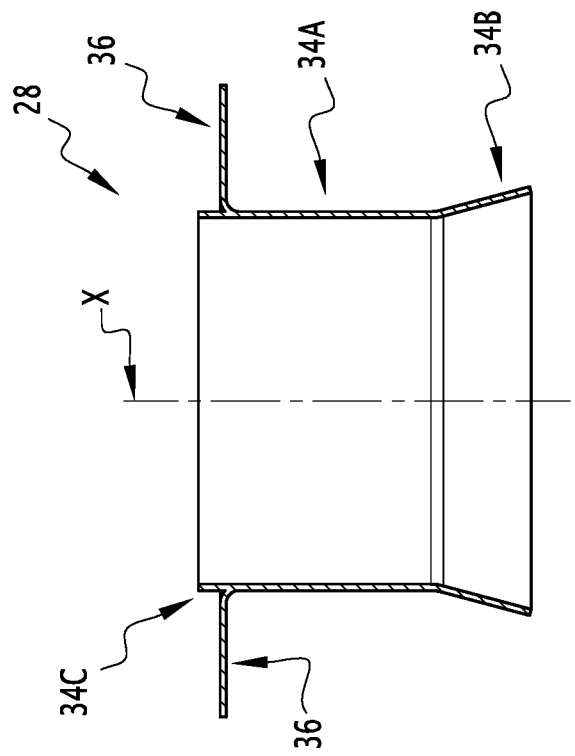
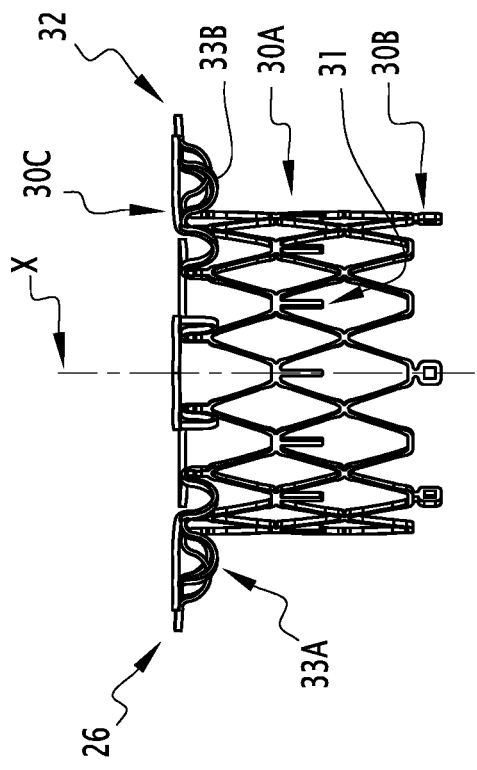
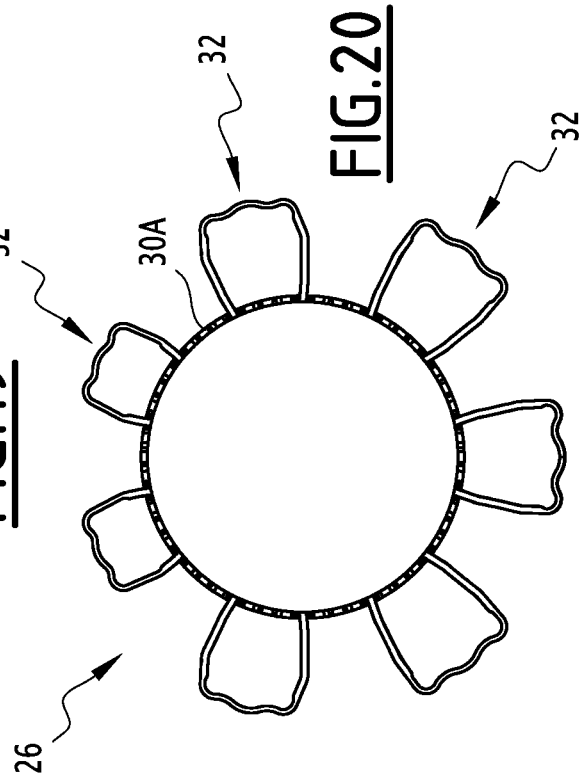

BIOLOGICAL VALVE TREATMENT DEVICE WITH PUSHING MEMBER OF THE VALVE

The present invention relates to a device for treating a biological valve including an implant having a proximal sleeve, deployable between a retracted configuration and a deployed configuration, intended to be positioned in a blood flow passage delimited by the valve, the proximal sleeve comprising a proximal tubular body and a plurality of proximal arms, each extending between a first end connected to the tubular body, and a second free end intended to bear on a first face of a leaflet of the valve or on an annulus of the valve, and a release tool for releasing the implant, extending longitudinally along a central axis between a proximal end and a distal end, the implant being mounted in the release tool in its retracted configuration.

The implant is in particular designed to replace a native heart valve, in particular a mitral valve. In the case of a mitral valve, the implant is designed to be placed in a blood passage of an atrioventricular valve of a human or animal heart.

During systole, the blood passage between the left atrium and the left ventricle of the heart is interrupted by the closing of a native heart valve present in a mitral apparatus. This valve ensures a unique circulation of the blood flow, avoiding reflux at the end of the ventricular contraction.

The mitral apparatus comprises a mitral annulus, two valvular leaflets connected to that annulus, and a sub-valvular apparatus comprising chords and pillars. The valvular leaflets include an anterior leaflet, also called "large mitral valve", and a posterior leaflet, also called "small mitral valve".

The connecting part connecting the annulus to the large mitral valve is fibrous, while the connecting part connecting the annulus to the small mitral valve is muscular. The small and large mitral valves are connected to the ventricular part by chords, which in turn are connected to the pillars. In diastole, the two leaflets open to free the passage between the left atrium and the left ventricle.

In systole, the ventricular contraction creates an abrupt elevation of the left intraventricular pressure, causing blood to be ejected through the aortic valve. At the same time, the contraction of the pillars and the tensing of the chords cause the junction of the leaflets with respect to one another, so as to tightly isolate the left atrial and ventricular cavities.

However, the valvular and sub-valvular mechanism may be affected by various pathologies, and in particular degenerative diseases responsible for regurgitation and mitral insufficiency.

Chronic mitral insufficiency is responsible for an expansion of the left ventricle and alterations of the ventricular function. In order to avoid this serious shift toward heart failure, it is necessary to reestablish valvular continence.

Reestablishing valvular function is done through valve replacement, by implanting an artificial valvular prosthesis in the atrioventricular orifice. This implantation can be surgical or transcatheter.

Transcatheter implantation of the valve is a less invasive technique than surgical valve replacement and may be offered to patients with a high surgical risk. In the case of a transcatheter solution, the implant for example includes a deployable tubular endoprosthesis and a flexible closing member made from animal tissue. The flexible closing member is permanently fastened in the endoprosthesis.

One example implant is described in WO 2014/170463.

Such an implant includes a central body provided with a plurality of atrial arms (also called "distal arms"), and a plurality of ventricular arms (also called "proximal arms") positioned across from the atrial arms to pinch the mitral annulus, while bearing on the atrial face of the leaflets of the native valve while plicating it. The ventricular arms are formed by hooks positioned at the ventricular end of the armature and folded toward the atrial end. The atrial arms are formed by V-shaped loops extending across from the ventricular arms, near the latter, but moving away from the armature and the atrial arms.

The ends of the ventricular arms and the atrial arms are positioned away from one another and are respectively engaged on an atrial face and a ventricular face of the mitral annulus.

It will be noted that the installation of a mitral implant to replace the native valve can be done by passing through the atrial cavity, or alternatively by passing through the ventricular cavity. This installation is generally done using an appropriate release tool. The structure of this release tool can be different depending on the side (atrial or ventricular) passed through to perform this installation.

The procedure to implant the mitral valve, and in particular the capture of the native valvular leaflets between the proximal and distal arms, may prove difficult, and consequently may be a source of implantation failure.

In particular, the positioning of the valve leaflets inside the receiving space created by all of the ventricular arms may prove difficult. Consequently, part of the valvular tissue may be situated outside the receiving space.

The invention in particular aims to facilitate the installation of a mitral implant, in particular while ensuring very effective fastening of the implant on the native valvular leaflets.

To that end, the invention in particular relates to a treatment device, wherein the device comprises a pushing member of the first face of the valve leaflet away from the free end of the proximal arms, the pushing member being movable along the direction of the central axis relative to the implant kept in its configuration retracted in the release tool between a withdrawn position and a deployed position pushing the first face of the valve leaflet.

A device according to the invention can further include one or more of the following features, considered alone or according to any technically possible combinations.

- the pushing member includes at least one deployable element, radially relative to the central axis of the release tool between a contracted state and a deployed state, the deployment of the deployable element being independent of the deployment of the implant;
- the deployable element in its deployed state comprises an outer pushing face oriented perpendicular to or distally separated from the central axis of the release tool;
- the proximal arms are movable radially between a configuration contracted in the release tool and a configuration deployed radially outside the release tool, the deployable element in its deployed state being received between or in front of the proximal arms in their radially deployed configuration;
- the deployable element comprises at least one lateral balloon inflatable independently of the configuration of the implant;
- the pushing member comprises at least two lateral balloons distributed symmetrically on either side of the central axis of the release tool;
- the lateral balloons are able to be inflated independently or simultaneously;
- the pushing member includes a deformable hollow tubular external sheath extending up to a distal end and having longitudinal slits distributed circumferentially, each pair of adjacent slits delimiting a deployable element, the pushing element including a rigid internal rod positioned inside the external sheath and connected to the distal end of the outer sheath, the external sheath being movable along the central axis relative to the inner rod to deploy the deployable elements by moving the inner rod relative to the outer sheath;

the number of deployable elements is greater than or equal to two;

a central balloon extended along the central axis of the release tool;

the pushing member includes an inner rod, with the same axis as the central axis of the release tool, inserted into the release tool, the deployable element being mounted at a distal end of the inner rod;

the release tool includes a tubular outer sheath movable relative to the proximal sleeve between a covering position of the proximal arms and a release position of the proximal arms, the pushing member being movable independently of the sheath;

the implant comprises a distal sleeve deployable between a retracted configuration and a deployed configuration intended to be positioned in the blood flow passage, comprising a distal tubular body able to be inserted into the proximal tubular body of the proximal sleeve of the implant;

the distal sleeve includes a plurality of distal arms each extending between a first end connected to the distal tubular body and a second free end intended to press on a second face of a leaflet of the valve opposite the first face or on the annulus of the valve;

the central balloon comprises an angular orientation device, including several marks, made from a radiopaque material, each mark being intended to assume an angular position, around the central axis of the implant, that is stationary relative to the implant, during the installation of the implant;

the implant comprises a proximal sleeve, deployable between a retracted configuration and a deployed configuration, the proximal sleeve comprising a proximal tubular body and a plurality of proximal arms, each extending between a first end connected to the proximal tubular body, and a second free end intended to bear on a first face of a leaflet of the valve or on an annulus of the valve and a distal sleeve, deployable between a retracted configuration and a deployed configuration, intended to be assembled with the proximal sleeve to form a tubular armature when the proximal sleeve and the distal sleeve are assembled, each in the deployed configuration, the distal sleeve comprising a distal tubular body and a plurality of distal arms intended to bear on the second face of the valve leaflet and/or the annulus, such that the valve leaflet and/or the annulus are pinched between the proximal arms and the distal arms;

each proximal arm protruding radially away from the proximal tubular body and defines a receiving space for the valve leaflet delimited by the proximal arm, with no participation of the tubular armature when the proximal sleeve and the distal sleeve are assembled;

the connected end of each proximal arm is connected to the distal end of the proximal sleeve;

each proximal arm extends along an axis substantially perpendicular to the central axis of the proximal sleeve, when there is no stress on the proximal arm, each proximal arm preferably having, with the central axis of the proximal sleeve, an angle comprised between 85° and 95°, when there is no stress on the proximal arm;

the free end of each proximal arm is positioned past a distal edge of the proximal body;

the receiving space is configured to prevent a valve leaflet received in the receiving space from coming into contact with the proximal tubular body of the proximal and distal sleeve;

the receiving space is defined by the proximal arm between its connected end and its free end, and in particular in an intermediate region of the proximal arm defining a trough for receiving a valve leaflet, the trough having a recessed concave shape, the trough being situated radially away from the proximal tubular body;

the trough has a U shape opening axially in a distal direction;

the trough includes a bottom, delimited between two parts of the intermediate region;

the bottom of the trough is situated beyond a distal edge of the proximal tubular body, along the central axis of the proximal sleeve;

each distal arm has a convex region, intended to be applied against the trough of the proximal arm on which the distal arm is attached;

the proximal sleeve includes an odd number of proximal arms;

the proximal arms are not diametrically opposite;

the proximal sleeve has, when it is separated from the distal sleeve, and when there is no outside stress, a diameter smaller than that of the distal sleeve without outside stress;

the distal tubular body has a cross-section at the proximal edge larger than its cross-section at the distal edge; this gradual increase in diameter being intended to ensure permanent gripping of the distal edge of the proximal tubular body toward the distal edge of the distal tubular body; and the proximal sleeve includes rods configured to be fastened in the distal sleeve, once assembled to one another, these rods being intended to secure the proximal sleeve to the distal sleeve.

The invention also relates to a method for treating a biological organ using a treatment device as described above, comprising the following steps:

inserting the release tool into the biological organ, moving the pushing member relative to a first face of a biological tissue of the biological organ, deploying the deployable element to its deployed configuration, pushing the first face of the tissue in the central axis of the release tool to a withdrawn position of the first face of the tissue, using the pushing member, keeping the first face of the tissue in the withdrawn position, deploying the proximal arms of the implant advantageously midway between the insertion of the chords and the papillary muscles, moving the implant into the vicinity of the first face of the tissue, and placing the proximal arms of the implant in contact with the first face of the tissue, contracting the pushing member into its contracted configuration.

The method according to the invention can further include one or more of the following features, considered alone or according to any technically possible combinations.

the pushing of the first face of the tissue arranges a deployment area for the proximal arms of the implant;

the method includes a step for radial pushing of the valve leaflets in the trough via the pushing member, during which the deployable element is deployed in the deployed configuration, such that the deployable element pushes the valve leaflets into the troughs of the proximal arms;

the leaflets housed in the trough form a seal around the tubular armature.

The invention will be better understood using the following description, provided solely as an example and done in reference to the appended figures, in which.

Figure 1:
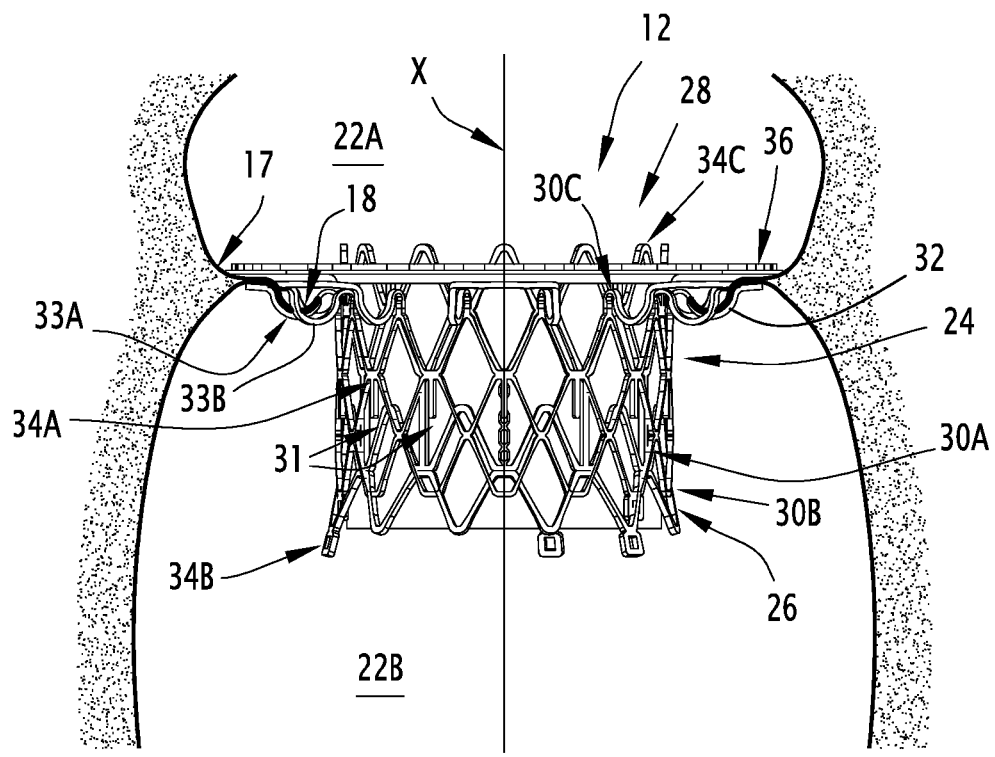
FIG. 1 is a schematic profile view of an implant positioned in a blood circulation passage, in a mitral valve.
Figure 12:
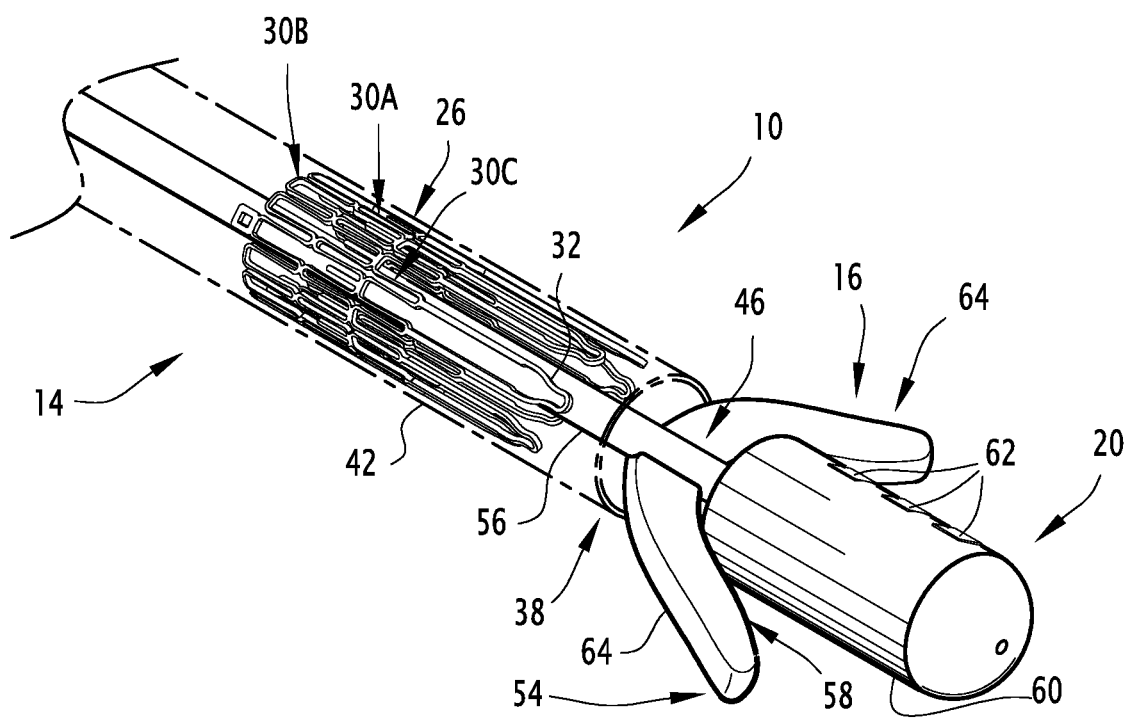
Figure 13:
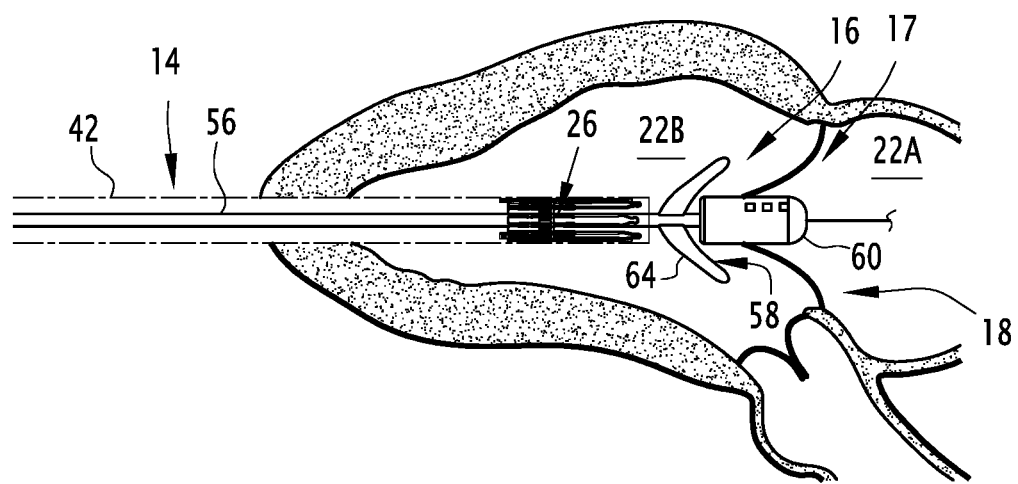
Figure 14:
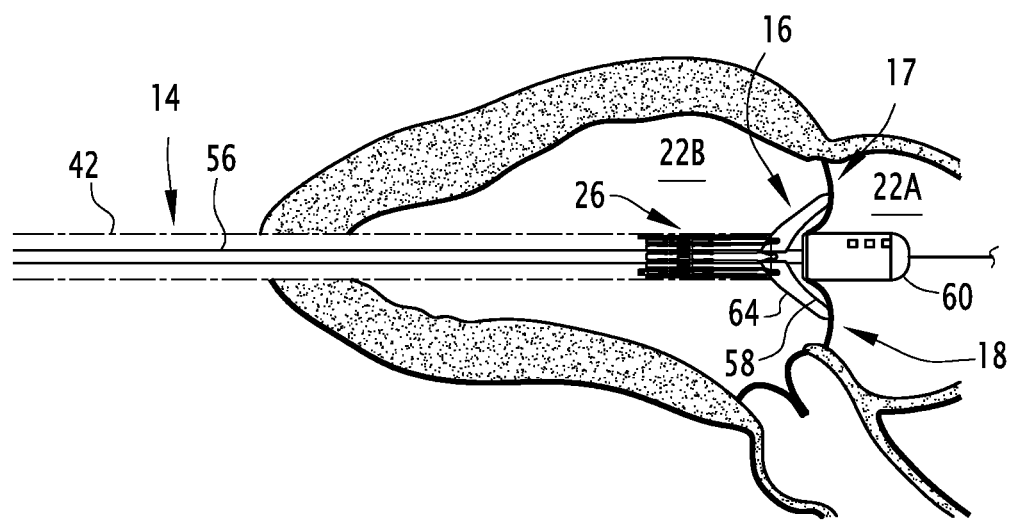
Figure 15:
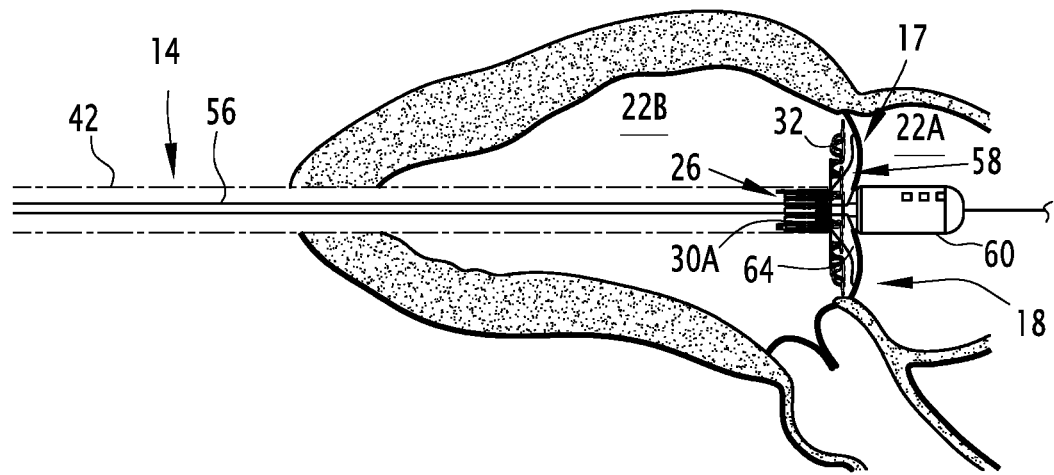
Figure 16:
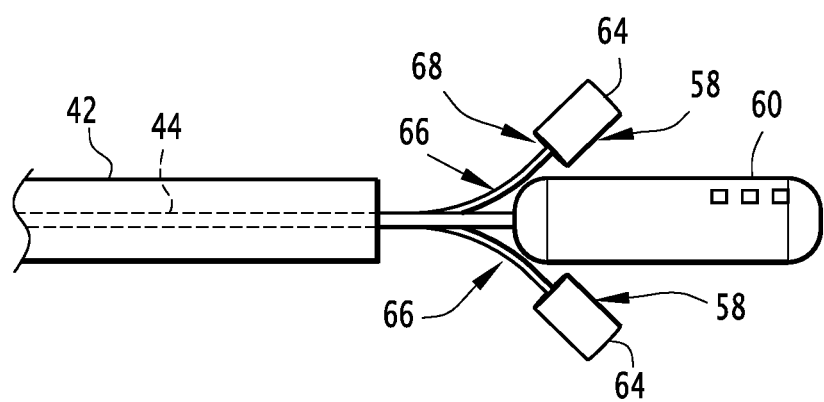
Figure 17:
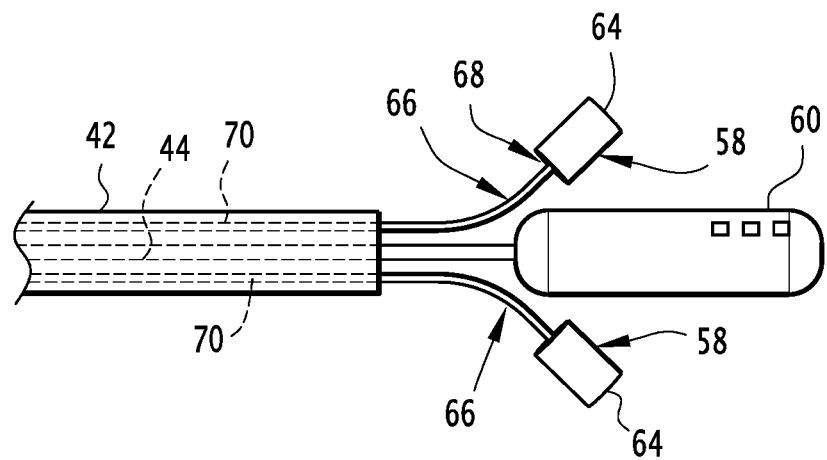
Figure 18:
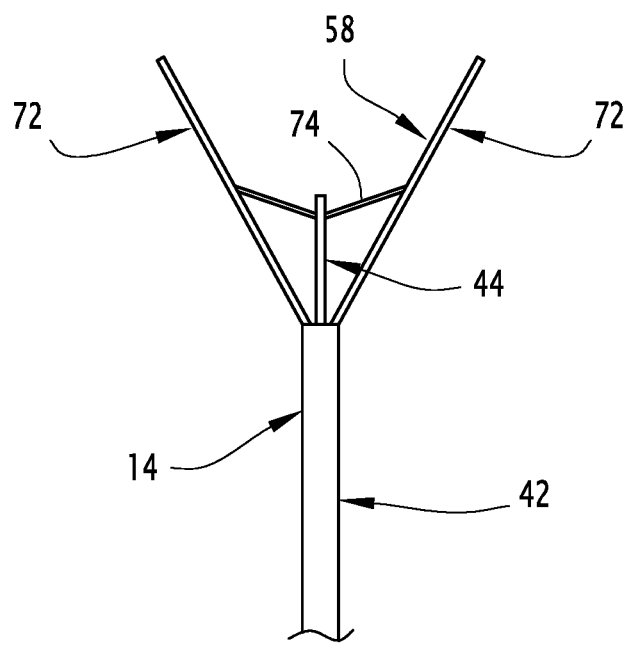

FIGS. 7 to 11 schematically show, in axial cross-section, a treatment device according to the first embodiment, shown in different release phases of the implant;

FIG. 12 is a perspective schematic view of the release tool according to a second embodiment of the invention;

FIGS. 13 to 15 schematically show, in axial cross-section, a treatment device according to the second embodiment, shown in different release phases of the implant;

FIGS. 16 and 17 are schematic views of the treatment device according to two other embodiments of the invention;

FIG. 18 is an axial sectional schematic view of the pushing member according to another embodiment of the invention;

FIG. 19 is a side view of the proximal sleeve of the implant of FIG. 1;

FIG. 20 is a top view of the proximal sleeve of the implant of FIG. 1; and

FIG. 21 is a side view of the distal sleeve of the implant of FIG. 1.

The figures show a device 10 for treating a biological organ, for example a heart valve defining a blood flow passage.

The treatment device 10 in particular includes an implant 12, intended to be positioned and deployed in the blood circulation passage of the heart, a release tool 14 for the implant 12, and a pushing member 16 movable longitudinally relative to the implant 12. The treatment device 10 here further includes an assembly 20 for producing an opening in a biological wall, here a wall of the heart.

The implant 12 is advantageously an endovalve, in particular a heart valve endovalve intended to replace a defective native valve. The endovalve is advantageously an endovalve designed to replace the native mitral valve situated between a left atrium 22A and a left ventricle 22B of the heart, so as to allow a unique circulation of the blood flow between the left atrium 22A and the left ventricle 22B visible in FIG. 1. The left ventricle 22B defines a ventricular cavity. The implant 12 is intended to be fastened on a tissue of the heart, this tissue in particular being formed by a mitral annulus 17 from which native mitral valve leaflets 18 are deployed.

Alternatively, the implant 12 is a valve intended to replace a native tricuspid valve or a native aortic valve.

The implant 12 shown in FIG. 1 includes a tubular armature 24, designed to define an inner blood flow conduit. The armature 24 is advantageously provided with a closing member (not shown) that is tissue-based, in particular synthetic or natural tissue, such as bovine, equine and/or porcine pericardium. This closing member is designed to ensure a unique circulation of the blood through this armature 24.

The tubular armature 24 includes a proximal sleeve 26 and a distal sleeve 28, intended to be attached in one another and assembled to form the armature 24. The distal sleeve 28 is thus intended to be deployed inside the proximal sleeve 26.

Figure 2:
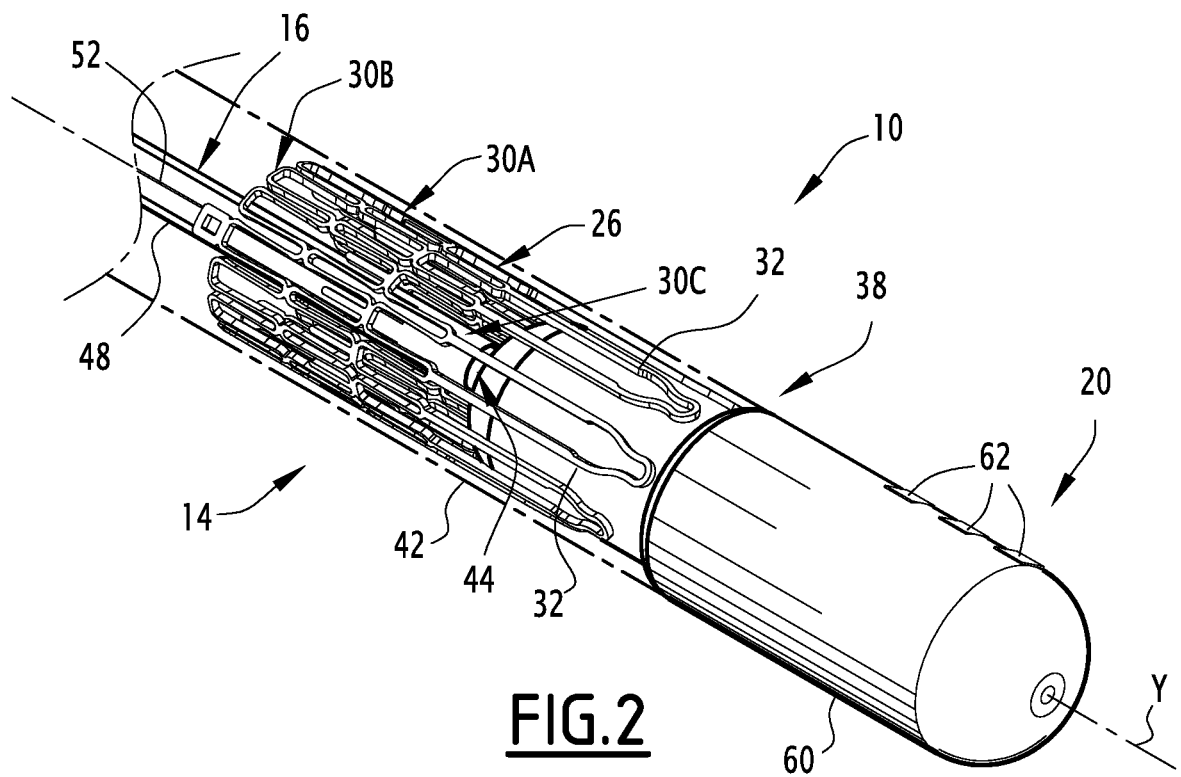
FIG. 2 is a perspective schematic view of the release tool according to a first embodiment of the invention.
Figure 3:
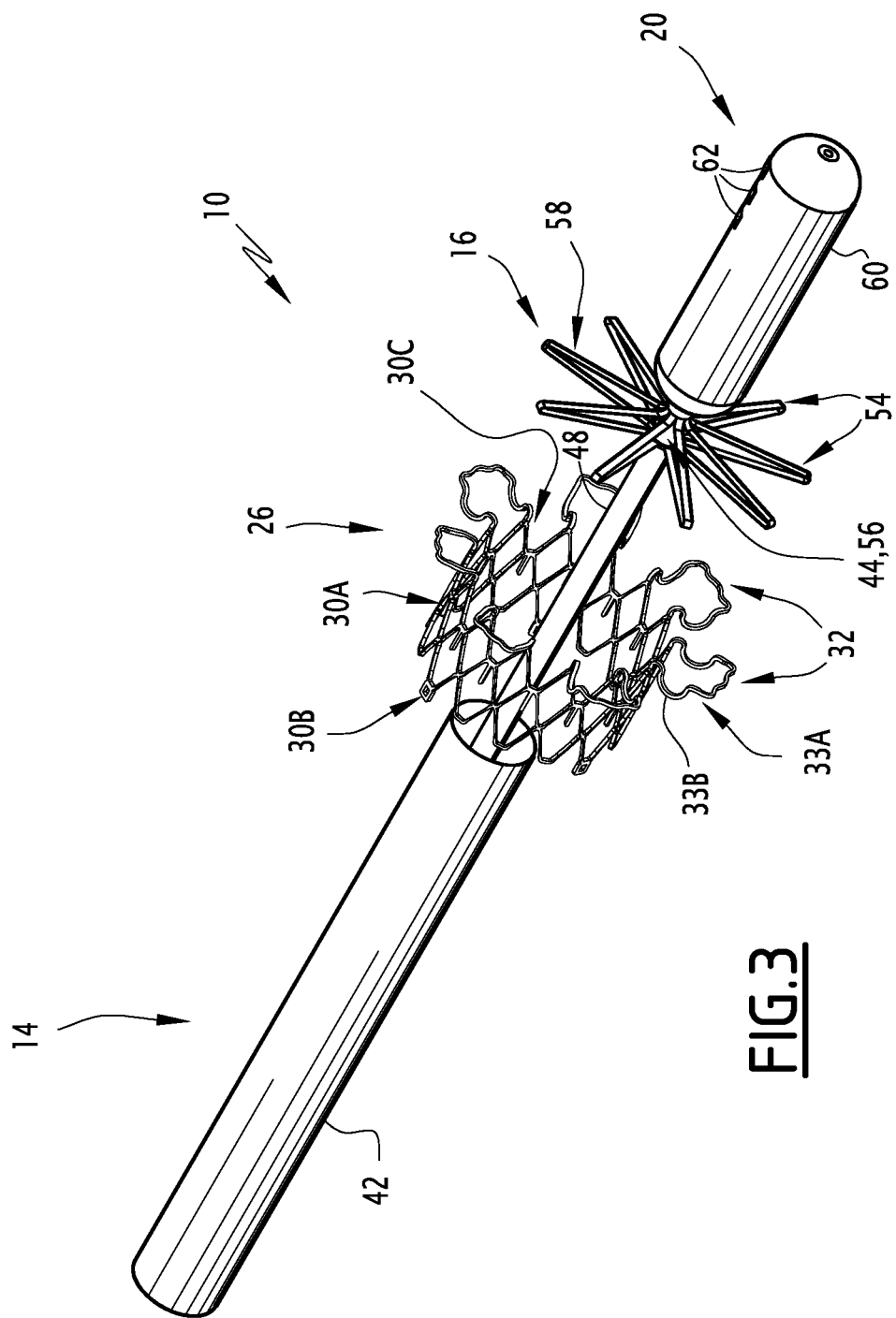
FIG. 3 is a schematic perspective view of the device according to the first embodiment in which the deployable elements of the pushing member and the proximal sleeve are deployed.

The proximal sleeve 26 includes a proximal tubular body 30A having a generally tubular shape around a central axis (X), and extending longitudinally, in the direction of this central axis (X), between a proximal edge 30B and a distal edge 30C The proximal sleeve 26 can be deployed between a retracted configuration shown in FIG. 2 and a deployed configuration visible in FIGS. 1 and 3.

The proximal sleeve 26 includes rods 31 configured to be fastened in the distal sleeve 28, once assembled to one another. These rods 31 are intended to secure the proximal sleeve 26 to the distal sleeve 28.

The implant 12 further includes a plurality of proximal arms 32, visible in FIG. 20, each protruding radially away toward the outside of the proximal sleeve 26 between a first end connected to the distal edge 30C of the proximal tubular body 30A of the proximal sleeve 26, and a second free end intended to bear on a first face of a valve leaflet 18 and/or on the mitral ring 17. The first face corresponds to the ventricular face of the valve leaflet 18.

The tubular proximal body 30A therefore forms, with the proximal arms 32, a first single-piece assembly. The proximal arms 32 being designed to press on the leaflet 18 and/or on the mitral annulus 17 of the valve on the left ventricle side 22B, these proximal arms 32 are also called "ventricular arms".

Each proximal arm 32 extends in a direction substantially perpendicular to the direction of the central axis (X). Advantageously, each proximal arm 32 has, with the central axis (X), an angle comprised between 85° and 95°, when there is no stress on the proximal arm 32. More specifically, each proximal arm 32 has, with the central axis (X), an angle such that its free end is positioned beyond the distal end 30C of the proximal tubular body 30A of the proximal sleeve 26. Each proximal arm 32 is formed by a closed wire forming a loop from the proximal tubular body 30A.

In the example of FIGS. 1 and 19, each proximal arm 32 includes, between its connected end and its free end, at least one intermediate region extending along and radially away from the armature 24, to define a longitudinal trough 33A for receiving a valve leaflet 18. The trough 33A creates a receiving space for the valve leaflets made up solely of the proximal arms 32, without participation by the proximal tubular body 30A of the proximal sleeve 26 or the distal tubular body 34A of the distal sleeve 28.

In FIG. 3, the trough 33A has a recessed concave shape.

The trough 33A includes a bottom 33B, delimited between two parts of the intermediate region situated radially separated from the proximal tubular body 30A or the distal tubular body 34A. The bottom 33B is intended to be arranged beyond the distal edge 30C of the proximal tubular body 30A, in the direction of the central axis (X), toward the proximal edge 30B of the proximal tubular body 30A, when the proximal sleeve 26 is in its deployed configuration.

The trough 33A has a U shape opening axially toward the distal sleeve 28. The trough 33A is connected to the proximal tubular body 30A by a transverse region of the arm forming an angle comprised between 85° and 95° with the central axis (X).

The trough 33A is positioned radially away from the proximal tubular body 30A.

The trough 33A is thus configured to prevent valve leaflets 18 received in the trough 33A from coming into contact with the proximal tubular body 30A of the proximal sleeve 26 or with the tubular body 34A of the distal sleeve 28.

The distal sleeve 28 includes a distal tubular body 34A, visible in FIG. 21, also having a general tubular shape around the central axis (X). The distal sleeve 28 is also deployable between a retracted configuration and a deployed configuration.

More particularly, this distal tubular body 34A is able to be inserted in the proximal tubular body 30A of the proximal sleeve 26. The distal sleeve 28 is thus intended to be assembled with the proximal sleeve 26 to form said tubular armature 24 of the implant 12 when this proximal sleeve 26 and this distal sleeve 28 are assembled, each in a deployed configuration.

The tubular body 34A extends longitudinally, in the direction of the central axis (X), between a proximal edge 34B and a distal edge 34C.

The distal tubular body 34A has a length, considered along the central axis (X), greater than the length of the proximal tubular body 30A, considered along the central axis (X).

The distal tubular body 34A has a cross-section at the proximal edge 34B, larger than its cross-section at the distal edge 34C. This difference in cross-section of the distal tubular body 34A makes it possible to push and immobilize the proximal tubular body 34A toward the distal edge 34C, when the proximal sleeve 26 and the distal sleeve 28 are assembled.

Advantageously, the proximal tubular body 30A of the proximal sleeve 26 has, when the proximal sleeve 26 is separated from the distal sleeve 28, and when there is no outside bias, a diameter smaller than that of the distal edge 34C of the distal tubular body 34A without outside stress. Thus, when the distal sleeve 28 is deployed inside the proximal sleeve 26, it exerts a radial force on an inner surface of the proximal sleeve 26, that radial force being sufficient to ensure the connection between the proximal sleeve 26 and the distal sleeve 28.

In reference to FIG. 1, the proximal sleeve 26 is intended to be positioned on the distal sleeve 28, such that the distal edge 30C of the proximal sleeve 26 is brought closer to the distal edge 34C of the distal sleeve 28, and for example radially aligned relative to the central axis (X) with this distal edge 34C.

The implant 12 also includes a plurality of distal arms 36, each being supported by the distal tubular body 34A of the distal sleeve 28 and extending substantially perpendicular to the central axis (X) when this distal sleeve 28 is in its deployed configuration. Thus, the distal tubular body 34A forms, with the distal arms 36, a second single-piece assembly, designed to be attached on the first assembly.

In one preferred embodiment, the distal arms 36 come together laterally to form a flange ring.

The distal arms 36 are intended to bear on a distal face of a valve leaflet 18 and/or the mitral annulus 17, i.e., on the side of the left atrium 22A, in the atrial cavity when the valve is a mitral valve. Thus, the distal arms 36 are also called "atrial arms".

When the implant 12 is installed in the blood flow conduit, advantageously, at least one distal end 36 is attached on a proximal arm 32. The valve leaflets 18 and/or the mitral ring 17 is (are) pinched between the proximal arms 32 and the distal arms 36, thus ensuring anchoring of the implant 12.

Advantageously, at least one, for example each, distal arm 36 has a convex region, intended to be applied against the trough 33A of the proximal arm 32 on which the distal arm 36 is attached. Alternatively, no distal arm 36 includes such a convex region.

It will be noted that this implant 12 is said to be "in the deployed configuration" when the proximal sleeve 26 and the distal sleeve 28 are assembled in the deployed configuration. Conversely, the implant 10 is said to be "in the retracted configuration" when the proximal 26 and distal 28 sleeves are positioned in retracted configurations.

The implant 12 for example has no plane of symmetry passing through the central axis (X). More specifically, the proximal sleeve 26 includes an odd number of proximal arms 32. The number of proximal arms 32 is also for example different from the number of distal arms 36. The proximal arms 32 are also advantageously not diametrically opposite. Furthermore, the distance between the connected end and the free end of each proximal arm 32 is different for each proximal arm 32, this distance depending on the shape of the valve leaflets 18.

Advantageously, each of the proximal 26 and distal 28 sleeves, therefore also the implant 12, is self-expanding, i.e., its deployed configuration is its idle position. Thus, each of the proximal 26 and distal 28 sleeves, therefore also the implant 10, in its retracted configuration, is elastically biased toward its deployed configuration.

For example, the proximal sleeve 26, the distal sleeve 28, the proximal arms 32 and the distal arms 36 are formed from a stainless steel having elastic properties. Alternatively, these elements are made with a base of a shape memory metal such as nitinol (nickel/titanium) or a flexible polymer fiber.

The proximal sleeve 26 is for example formed by a lattice of interlaced filiform elements, defining cells, for example polygonal cells, preferably diamond-shaped cells visible in the figures.

Likewise, the distal sleeve 28 is for example formed by a lattice of interlaced filiform elements, defining cells, for example polygonal cells, preferably diamond-shaped cells visible in the figures.

In one embodiment of the release of the implant 12, illustrated in the figures, the proximal sleeve 26 and the distal sleeve 28 are brought into the blood circulation passage via two separate access routes. More specifically, the distal sleeve 28 is brought by the transvenous antero-grade route, and thus inserted into the atrial cavity without passing through the ventricular cavity, and the proximal sleeve 26 is brought by the transaortic retrograde route, and thus is inserted into the ventricular cavity without passing through the atrial cavity.

The treatment device 10 thus includes a first release tool 14 for the proximal sleeve 26 and a second release tool (not shown) for the distal sleeve 28.

The first release tool 14, in particular visible in FIGS. 2 and 3, extends longitudinally along a central axis (Y) between a proximal end (not shown) and a distal end 38. It advantageously includes a guide wire 40 (visible in FIGS. 7 to 11), an outer sheath 42 forming a hollow tubular element with a substantially circular cross-section and an inner rod 44 positioned in the outer sheath 42 movable along the guide wire 40 and extending between a proximal end and a distal end.

The inner rod 44 is movable relative to the outer sheath 42 along the central axis (Y).

The guide wire 40 is for example shared by the first release tool 14 and the second release tool.

Locking elements (not shown) are generally provided between the rod 44 and the outer sheath 42, to avoid spontaneous sliding of these elements relative to one another.

As shown in particular in FIG. 2, the outer sheath 42 delimits, with the inner rod 44, an inner annular space receiving the proximal sleeve 26. Thus, the proximal sleeve 26 is kept in the retracted configuration by this outer sheath 42.

When the proximal sleeve 26 is in the retracted configuration in the first release tool 14, the central axis (X) of the proximal sleeve 26 is substantially combined with the central axis (Y) of the first release tool 14.

Furthermore, each proximal arm 32 is pressed against the outer sheath 42 as long as it is covered by this outer sheath 42.

The proximal arms 32 are movable radially between a configuration contracted in the release tool and a configuration deployed radially outside the release tool 14.

The tubular outer sheath 42 is movable relative to the proximal sleeve 26 along the central axis (Y) between a covering position of the proximal arms 32 and the proximal sleeve 26, an intermediate position for deployment of the proximal arms 32 in which the proximal sleeve 26 is still covered by the outer sheath 42, and a release position of the proximal sleeve 26.

The second release tool also extends longitudinally along a second central axis between a proximal end and a distal end.

This second release tool has characteristics similar to the first release tool 14. Thus, the second release tool includes at least an outer sheath, an inner rod positioned in this outer sheath and members for locking the movements of these elements relative to one another; the outer sheath of the second release tool delimits an inner annular space intended to receive the distal sleeve 28 that is kept in the retracted configuration by this outer sheath. Likewise, each distal arm 36 is pressed against the outer sheath of the second release tool as long as it is covered by this outer sheath. The distal arms 36 are thus movable radially between a configuration contracted in the second release tool and a configuration deployed radially outside the second release tool.

The second release tool is for example similar to that described in WO 2014/170463, FIGS. 29 to 32.

The treatment device 10 further includes a pushing member 16 for pushing the first face of the valve leaflet 18 away from the distal end 38 of the release tool 14. The pushing member 16 is inserted in the release tool 14, as illustrated in FIG. 2.

The pushing member 16 is movable along the direction of the central axis (Y) relative to the outer sheath 42 and relative to the implant 12 kept in its configuration retracted in the release tool 14, more specifically relative to the proximal sleeve 26 in the embodiment of the figures, between a withdrawn position and a deployed position pushing the first face of the valve leaflet 18.

In the withdrawn position of the pushing member 16, the outer sheath 42 covers the pushing member 16, as illustrated in FIG. 2.

Figure 4:
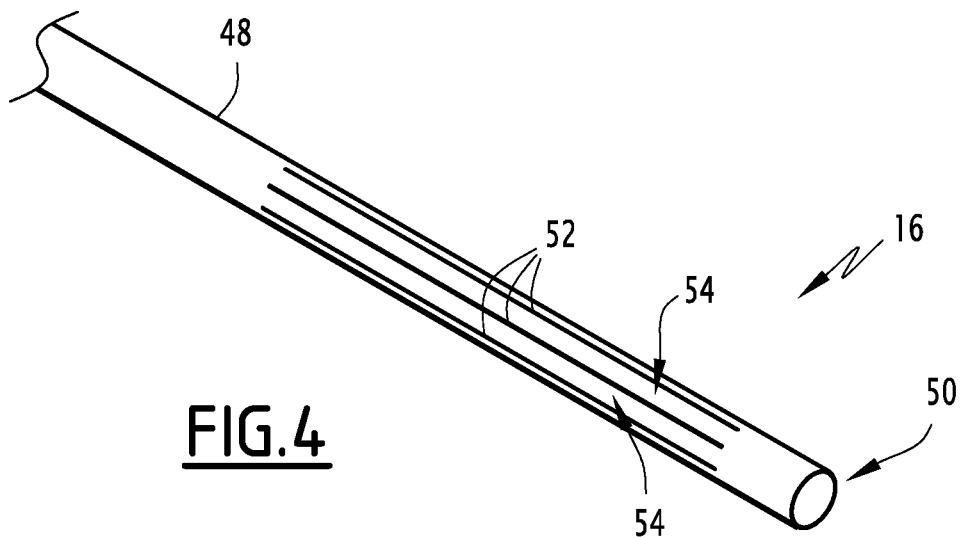
FIG. 4 is a schematic perspective view of the first embodiment of the pushing member in which the deployable elements are in the contracted state.
Figure 5:
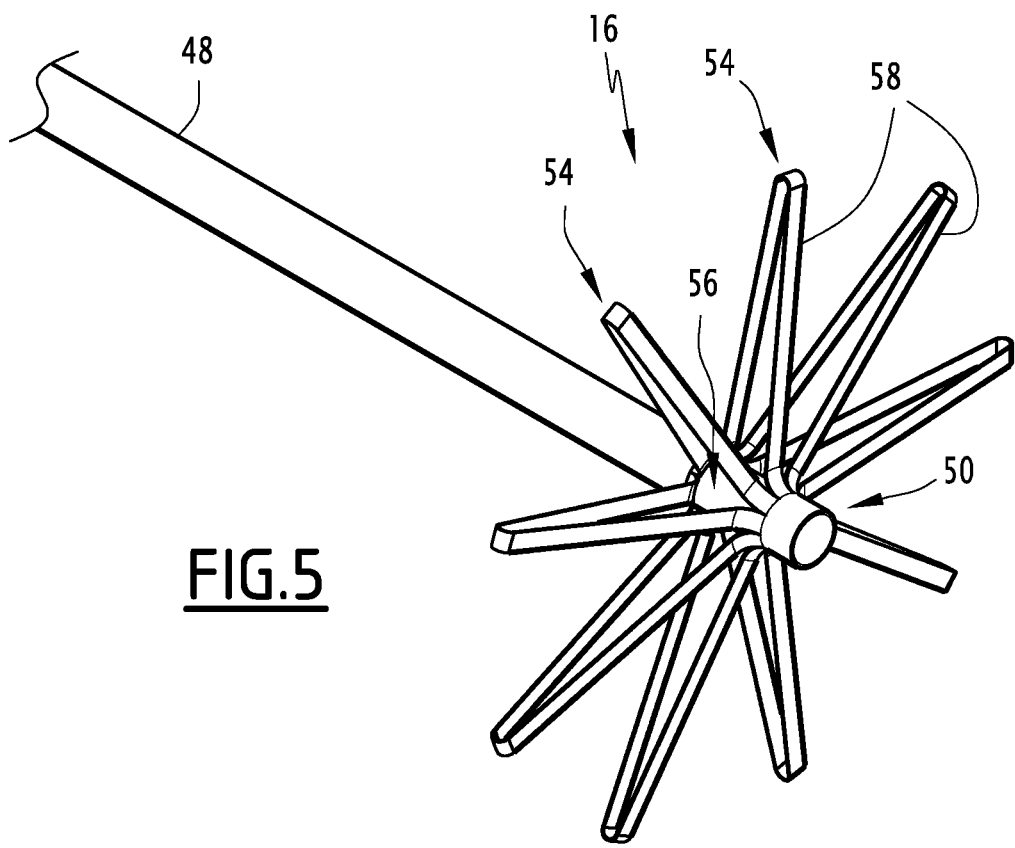
FIG. 5 is a schematic perspective view of the first embodiment of the pushing member in which the deployable elements are in the deployed state.
Figure 6:
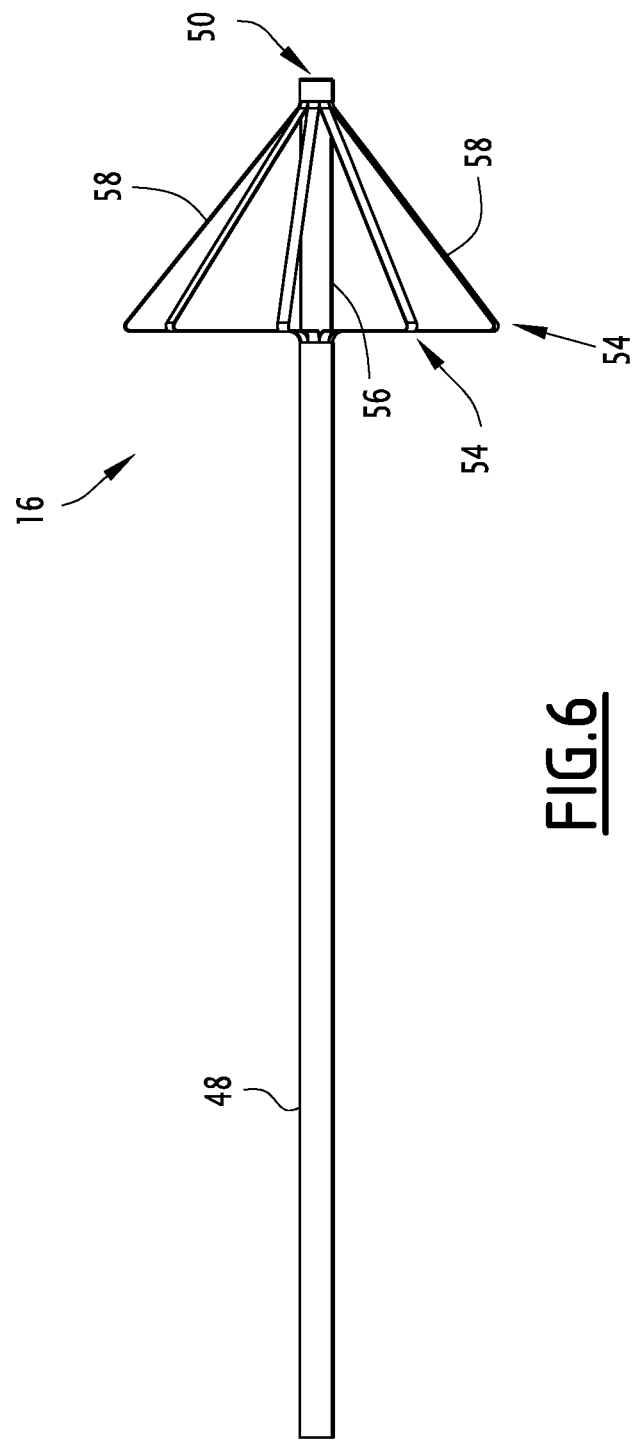
FIG. 6 is a schematic axial sectional view of the pushing member, in which the deployable elements are between the deployed state and the contracted state.

In a first embodiment illustrated in FIGS. 2 to 11, the pushing member 16 includes a deformable hollow tubular external sheath 48 extending to a distal end 50. As illustrated in FIGS. 4 to 6, the external sheath 48 has longitudinal slits 52 distributed circumferentially, each pair of adjacent slits 52 delimiting a deployable element 54.

The number of deployable elements 54 is for example greater than or equal to two.

The pushing member 16 further includes a rigid inner rod 56 with the same axis as the central axis (Y), positioned inside the external sheath 48 and connected to the distal end 50 of the external sheath 48.

The rigid inner rod 56 is for example the inner rod 44 of the first release tool 14. Alternatively, the rigid inner rod 56 is hollow, the inner rod 44 of the first release tool 14 then being positioned inside the rigid inner rod 56 and movable relative to the rigid inner rod 56 along the central axis (Y) of the release tool 14.

The external sheath 48 is movable along the central axis (Y) relative to the rigid inner rod 56 to deploy the deployable elements 54 by the movement of the rigid inner rod 56 toward the proximal end of the release tool 14 relative to the external sheath 48.

This deployment is carried out after the pushing member 16 has been moved outside the release tool 14, the outer sheath 42 no longer covering the pushing member 16.

During this deployment, a first end of the deployable element 54, in particular the distal end of the deployable element 54, remains stationary relative to the rod 56, while a second end, in particular the proximal end of the deployable element 54, is movable relative to the first end to come closer to the first end. The deployable element 54 bends in its median part and forms a radially deployed elbow.

Each deployable element 54 is thus deployable, independently of the deployment of the implant 12, radially relative to the axis of the first release tool 14 between a contracted state illustrated in FIG. 4 and a deployed state illustrated in FIGS. 3 and 5.

In the contracted state, each deployable element 54 is able to slide in the proximal sleeve 26 in the retracted or deployed configuration, so as to allow the withdrawal of the pushing member 16 during the installation of the implant 12, for example prior to the insertion of the distal tubular body 34A of the distal sleeve 28 into the proximal tubular body 30A of the proximal sleeve 26.

In the deployed state, each deployable element 54 comprises an outer pushing face 58 oriented perpendicular to the central axis (Y) of the release tool 14.

In the deployed state, as illustrated in FIGS. 5 and 6, the radially deployed elbow of each deployable element 54 advantageously has an end, intended to push the leaflets 18 radially into the troughs 33A of the proximal arms 32.

By moving the pushing member 16, relative to the release tool 14 and the implant 12 and along the central axis (Y) of the release tool 14, each outer pushing face 58 is able to push the first face of the valve leaflet 18 away from the distal end 38 of the release tool 14 to arrange a deployment area of the proximal arms 32 of the proximal sleeve 26.

Thus, after the radial deployment of the proximal arms 32 outside the release tool 14, each deployable element 54 in its deployed state is received in the receiving trough 33A defined by the proximal arms 32.

Each deployable element 54, in its deployed state, is thus able to be received in front of or between the proximal arms 32 in their radially deployed configuration.

The assembly 20 for producing an opening is able to arrange and widen the passage at the tip of the left ventricle 22B, for the passage of the first release tool 14 in the left ventricle 22B. The assembly 20 for producing an opening is arranged in front of the sleeve 26 and the pushing member 16.

The assembly 20 for producing an opening comprises a cutting or perforating element (not shown) able to make an incision or perforation in the wall of the heart.

The assembly 20 for producing an opening includes a central balloon 60 positioned at the distal end of the inner rod 44 of the release tool 14. The central balloon 60 has a substantially circular cross-section, inflatable between a deflated configuration, in which the central balloon 60 is able to be inserted in a puncture made in the heart wall, and an inflated configuration, in which the central balloon 60 has a predetermined diameter corresponding to the diameter of the opening to be made. The central balloon 60 is arranged at the distal end 16 of the inner rod 44 of the first release tool 14.

The predetermined diameter of the central balloon 60 in the inflated configuration is greater than or equal to the diameter of the outer sheath 42.

In the inflated configuration, the central balloon 60 extends partly in the inner space delimited by the outer sheath 42, and partly beyond a distal end of the outer sheath 42. Thus, the central balloon 60 in the inflated configuration is firmly maintained, under the effect of its internal pressure, at the outer sheath 42, as in particular shown in FIG. 2.

Conversely, the central balloon 60 is able to slide in the outer sheath 42 in the deflated configuration, more particularly in the proximal sleeve 26 in the retracted configuration, so as to allow the withdrawal of the central balloon 60 during the installation of the implant 12, for example prior to the insertion of the distal tubular body of the distal sleeve 28 into the proximal tubular body 30A of the proximal sleeve 26.

Advantageously, the central balloon 60 is filled with a radiopaque material. Its evolution, in particular its position, is thus observable by x-ray.

As illustrated in FIG. 2, the central balloon 60 also comprises an angular orientation device including several marks 62, made from a radiopaque material. Here, the marks 62 are separated, aligned along the central axis (Y) of the release tool 14 and applied on the central balloon 60.

The marks 62 are for example metal.

Each mark 62 is intended to assume an angular position around the central axis (X) of the implant, that is stationary relative to the implant 12, during the installation of the implant 12 on the valve.

The main steps of a method for treating a blood flow passage of a mitral valve, using the treatment device 10 illustrated by FIGS. 1 to 2, will now be described.

The treatment method includes a step for producing a puncture in the heart wall, in particular at the tip of the left ventricle 22B, using the cutting or perforating element of the assembly 20 for producing an opening. Alternatively, the incision or perforation can be made on another point of entry of the heart, in particular on a part of the left ventricle 22B other than the tip, on the left atrium 22A, on the right ventricle, on the right atrium.

Figure 7:
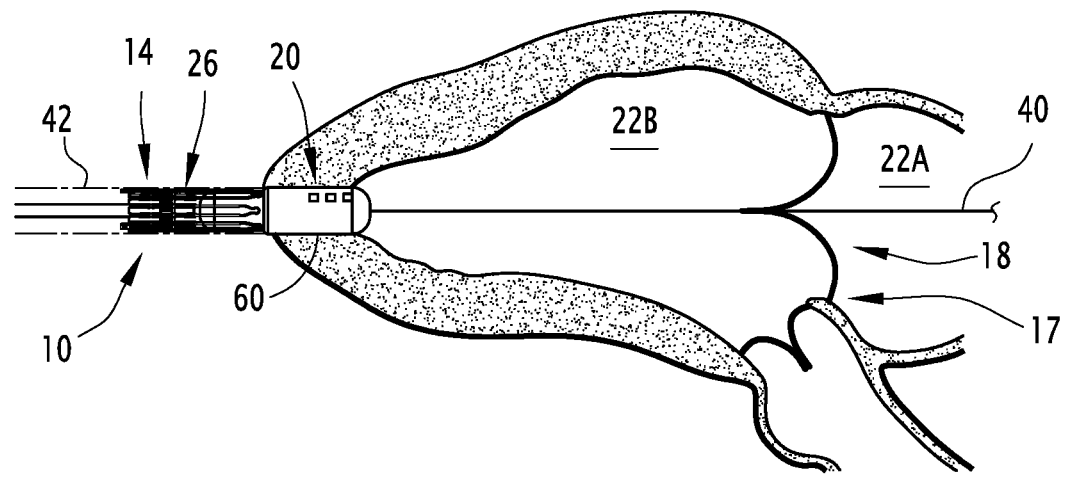

The method next includes a step for inserting the central balloon 60 into the incision or perforation that has been produced and a step for enlarging the incision or perforation so as to produce an opening, by inflating the central balloon 60. Such a step is illustrated in FIG. 7 and is for example described in document FR 3,002,084.

The method next includes a step for inserting the release tool 14 into the ventricular cavity, more specifically into the left ventricle 22B, by moving this release tool 14 through the produced opening.

It will be noted that the central balloon 60 being made from a radiopaque material, it is possible to observe its proper evolution in the left ventricle 22B. Via the marks 62, it is in particular possible to monitor its angular evolution around the central axis (Y).

The release tool 14 is next advanced toward the left atrium 22A, guided by the guide wire 40, such that the proximal sleeve 26 in the retracted configuration is positioned at a distance from the valve leaflets 18 in the left ventricle 22B.

The central balloon 60 is at least partially deflated.

Figure 8:
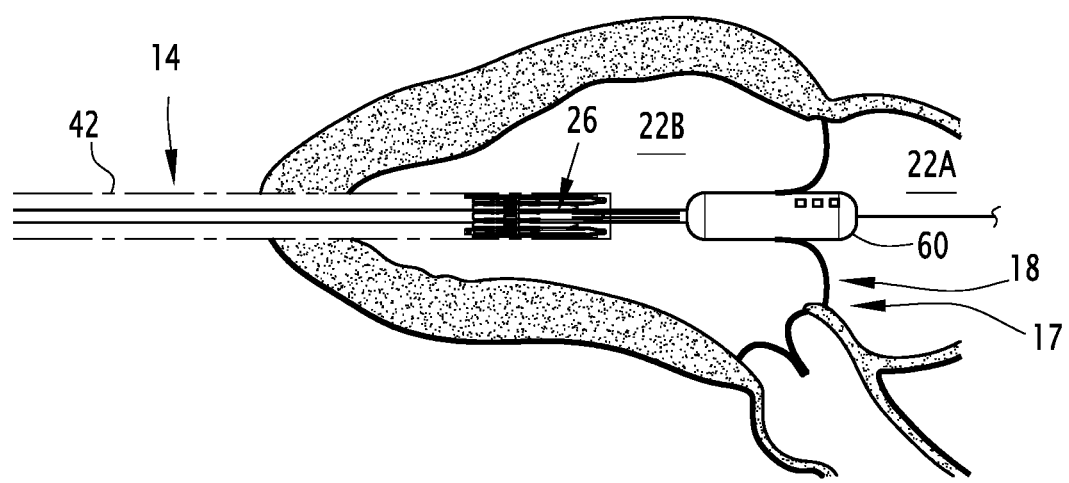
Figure 9:
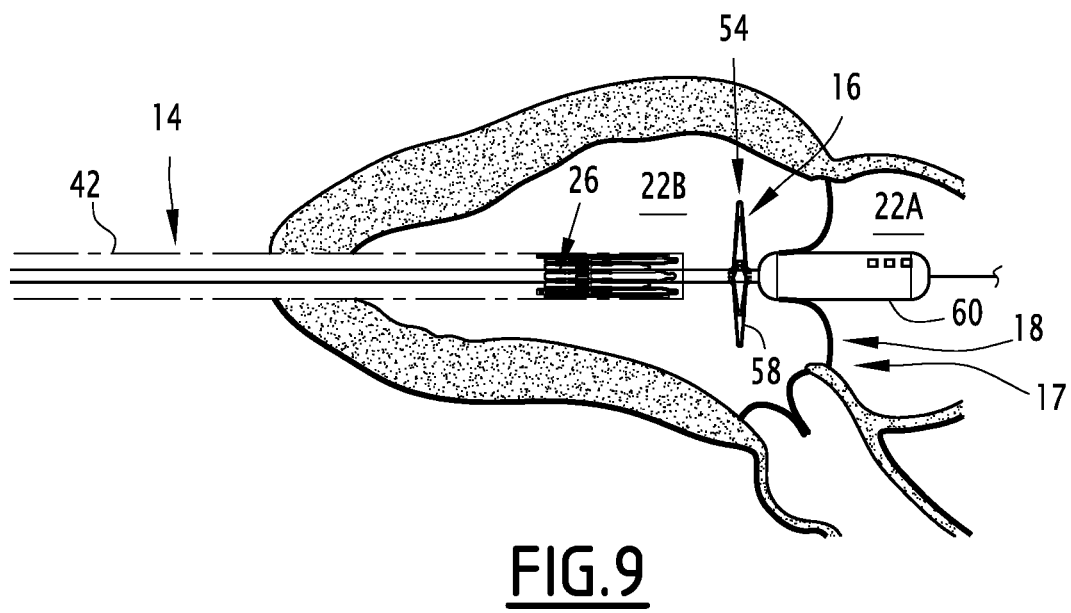

As shown in FIG. 8, the central balloon 60 and the pushing member 16 are moved relative to the outer sheath 42 of the release tool 14 toward the mitral valve. The central balloon 60 is then positioned in the mitral valve and the pushing member 16 is thus exposed outside the outer sheath 42.

The method then includes a step for deploying each deployable element 54 of the pushing member 16. During this step, illustrated by FIG. 9, the rigid inner rod 56 of the pushing member 16 is kept in position while the hollow tubular external sheath 48 is moved toward the distal end 38 of the release tool 14. Each deployable element 54 then goes from the contracted state to the deployed state.

More specifically, a first end of the deployable element 54, in particular the distal end of the deployable element 54, remains stationary relative to the rod 56. A second end, in particular the proximal end of the deployable element 54, comes closer to the first end. The deployable element 54 bends in its median part and forms a radially deployed elbow.

Alternatively, the deployment of each deployable element 54 is done while keeping the hollow tubular external sheath 48 in position and moving the rigid inner rod 56 of the pushing member 16 toward the proximal end of the release tool 14.

The method next includes a step for pushing the first valve leaflet 18 face. The pushing member 16 is moved in the central axis (Y) of the release tool 14 until each outer pushing face 58 comes into contact with the first face of the valve leaflet 18. An additional movement of the pushing member 16 in the central axis (Y) of the release tool 14 allows each outer pushing face 58 to push the valve leaflet 18 to a withdrawn position, away from the distal end 38 of the release tool 14, thus arranging a clear deployment area for the proximal arms 32 and the proximal sleeve 26.

The valve leaflet 18 is kept in its withdrawn position by the pushing member 16 at least to the position of the proximal arms 32 below the first face of the leaflet 18.

The method next comprises a step for deployment of the proximal arms 32, during which the outer sheath 42 is moved axially toward the proximal end of the release tool 14 from its covering position to its intermediate deployment position of the proximal arms 32.

The proximal arms 32 are then radially deployed in the cleared deployment area, the proximal sleeve 26 still being covered by the outer sheath 42. The proximal arms 32 thus pass between the chords of the sub-valvular mechanism.

Figure 10:
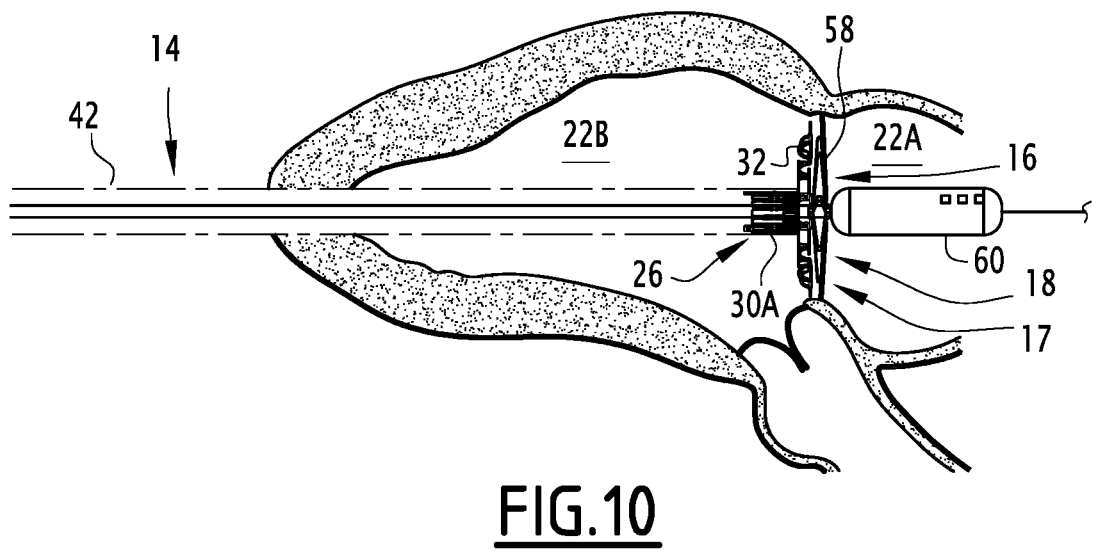

The proximal arms 32 deployed outside the outer sheath 42 and the proximal sleeve 26 received in the outer sheath 42 are next advanced toward the mitral annulus such that the receiving trough 33A defined by the proximal arms 32 is positioned across from the deployable elements 54. The deployable elements 54 are thus received between the valvular leaflets 18 and the proximal arms 32, as shown in FIG. 10.

The marks 62 assuming a predefined angular position around the central axis (Y) that is stationary relative to the sleeve 26, the proximal arms 32 are carefully angularly positioned around the central axis (Y), relative to the first face of the leaflet 18 and/or the mitral annulus 17.

The proximal arms 32 are advanced in contact with the first face of the leaflet 18 and/or the mitral annulus 17, the pushing member 16 and the valve leaflets 18 being positioned on top of the receiving troughs 33A defined by the proximal arms 32.

The proximal arms 32 apply an axial force against the ventricular face of the leaflets 18 and/or the mitral annulus 17, this axial force being oriented from the ventricular cavity toward the atrial cavity.

This being done, when the position of the proximal arms 32 is deemed adequate by the practitioner, the central balloon 60 is deflated. The central balloon 60 and the pushing member 16 are advanced outside the vicinity of the mitral valve in the left atrium 22A.

Likewise, each deployable element 54 of the pushing member 16 is contracted, by keeping the rigid inner rod 56 in position and moving the hollow tubular external sheath 48 of the pushing member 16 toward the proximal end of the release tool 14.

Alternatively, the contraction of each deployable element 54 is done while keeping the hollow tubular external sheath 48 in position and moving the rigid inner rod 56 of the pushing member 16 toward the distal end 38 of the release tool 14.

Figure 11:
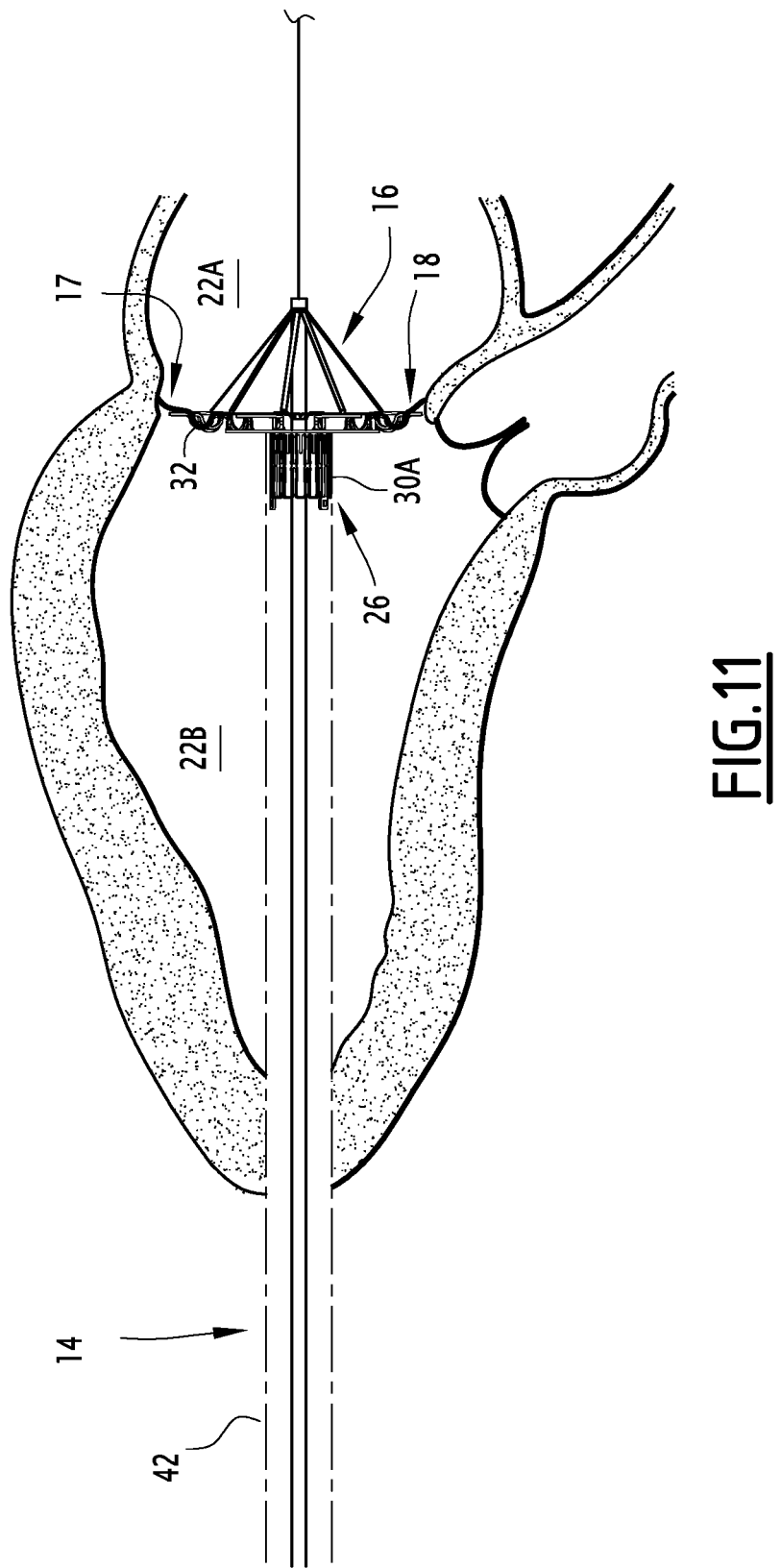

As illustrated in FIG. 11, the method then includes a step for radial pushing of the valve leaflets 18 in the trough 33A by the pushing member 16.

After the contraction of each deployable element 54, the leaflets 18 rest on the proximal arms 32. The deployable elements 54 of the pushing member 16 are then deployed again in the left atrium 22A. During this deployment, the conical end elbows of the deployable elements 54 push the valve leaflets 18 into the troughs 33A of the proximal arms 32.

The leaflets 18 then form a seal around the implant 12 on the ventricular side and near the annulus 17, thus closing a commissural space.

The deployable elements 54 are next contracted and the pushing member 16 is moved toward the proximal end of the release tool 14. The central balloon 60 is then also moved toward the proximal end of the release tool 14.

In this embodiment, simultaneously with or following one of the previous steps, the method includes a step, not shown, for introducing a second release tool into the atrial cavity via a second route different from that by which the first release tool 14 was inserted into the ventricular cavity.

After the removal of the central balloon 60 and the pushing member 16, and by moving the second release tool, the distal sleeve 28 in the retracted configuration is moved to the left ventricle 22B such that the distal arms 36, still in the contracted configuration, are positioned in the left atrium 22A. The distal tubular body of the distal sleeve 28 is thus inserted in the proximal tubular body 30A of the proximal sleeve 26.

The method next includes a step, not shown, for deploying the distal arms 36 during which the distal sleeve 28 is kept in the retracted configuration. The distal arms 36 are deployed and applied on the second face of the valve leaflets 18 and/or the mitral annulus 17 corresponding to the atrial face of the valve leaflet 18 and/or the mitral annulus 17, the distal sleeve 28 retaining its retracted configuration.

Thus, the distal arms 36 apply an axial force against the atrial face of the leaflets 18 and/or the mitral annulus 17, this axial force being oriented from the atrial cavity toward the ventricular cavity. The axial force applied by the proximal arms 32 is in substantially the same direction but the opposite way with respect to the axial force applied by the distal arms 36.

The positions of the proximal sleeve 26 and the distal sleeve 28 are adjusted based on the configuration of the blood circulation passage in which the implant 12 is installed.

When the positions of the proximal sleeve 26 and the distal sleeve 28 are deemed adequate by the practitioner, the outer sheath 42 is moved toward its released position of the proximal sleeve 26, and the proximal sleeve 26 is released. It is deployed radially outside the release tool 14.

Next, the distal sleeve 28 positioned in the proximal sleeve 26 is deployed.

Alternatively, the proximal sleeve 26 and the distal sleeve 28 are deployed simultaneously, or the distal sleeve 28 is deployed inside the proximal sleeve 26 prior to the deployment of the proximal sleeve 26.

After the deployment of the distal sleeve 28, the proximal 26 and distal 28 sleeves are assembled by radio contact, thus forming the armature 24. In other words, the armature 24 is only formed in the deployed configuration.

Once these deployments are done, the first and second release tools are removed from the patient, each through the corresponding approach.

In another embodiment, the proximal sleeve 26 and the distal sleeve 28 are brought into the blood circulation passage via the transapical (apex of the heart) approach using the same release tool 14. The release tool 14 then includes, before the releases, the proximal sleeve 26 and the distal sleeve 28 in the retracted configurations, as described in WO 2014/170463, FIGS. 21 to 24. Until the deployment of the proximal arms 32 and the radial pushing of the valve leaflets 18 in the trough 33A by the pushing member 16, the associated treatment method comprises the same steps as that previously described. Then, the distal sleeve 28 is released from the release tool 14 by passing it through the proximal tubular body 30A.

In another variant, the proximal sleeve 26 and the distal sleeve 28 are brought into the blood flow passage via a transseptal transfemoral approach by transvenous anterograde approach and are thus inserted into the atrial cavity without passing through the ventricular cavity by using the same release tool 14.

Until the deployment of the proximal arms 32 and the radial pushing of the valve leaflets 18 in the trough 33A by the pushing member 16, the associated treatment method comprises the same steps as that previously described, except that during the step for pushing the first valve leaflet 18 face, each outer face 58 pushes the valve leaflet 18 to a withdrawn position of the proximal arms 32, toward the distal end 38 of the release tool 14.

A second embodiment of the treatment device 10, in particular of the pushing member 16, is described in FIGS. 12 to 15.

In the example of FIG. 12, the pushing member 16 has been removed from the tubular outer sheath 42.

As illustrated in this figure, the pushing member 16 includes a rigid rod 56 and several deployable elements 54 each comprising an inflatable lateral balloon 64. Each lateral balloon 64 is positioned at the distal end 38 of the release tool 14 and is connected to the rigid inner rod 56.

In FIG. 12, the pushing member 16 includes two deployable elements 54. The two lateral balloons 64 are distributed symmetrically on either side of the central axis (Y) of the release tool 14.

The rigid inner rod 56 is hollow, the inner rod 44 of the first release tool 14 then being positioned inside the rigid inner rod 56 and movable relative to the rigid inner rod 56 along the central axis (Y) of the release tool 14.

Each lateral balloon 64 is inflatable independently of the configuration of the implant 12, and in particular independently of the configuration of the proximal sleeve 26. Thus, each lateral balloon 64 is deployable radially relative to the central axis (Y) of the release tool 14 between a contracted state (not shown) corresponding to a state where the lateral balloon 64 is deflated, and a deployed state shown in FIG. 12, corresponding to a state where the lateral balloon 64 is inflated.

The lateral balloons 64 being connected to the same rigid inner rod 56, they are able to be inflated simultaneously.

In the contracted state of each lateral balloon 64, i.e., when it is deflated, the lateral balloon 64 is able to be kept in the outer sheath 42 of the release tool 14.

Furthermore, each lateral balloon 64 is, in its contracted state, movable relative to the proximal sleeve 26 along the central axis (Y) of the release tool 14, to be able to slide in the proximal sleeve 26 in the retracted or deployed configuration, so as to allow the withdrawal of the pushing member 16 during the installation of the implant 12, for example prior to the insertion of the distal tubular body of the distal sleeve 28 into the proximal tubular body 30A of the proximal sleeve 26.

Each lateral balloon 64 comprises, in its deployed state, an outer pushing face 58 oriented perpendicular to or distally separated from the central axis (Y) of the release tool 14. Each lateral balloon 64 also comprises, in its deployed state, a second outer face, advantageously intended to push the leaflets 18 radially in the troughs 33A of the proximal arms 32.

A method for treating a blood flow passage of a mitral valve, using the treatment device 10 according to this second embodiment, will now be described. In the following description, only the steps that are different from the method previously described are illustrated and described in detail.

Before the step for deploying each deployable element 54 and as illustrated in FIG. 13, the pushing member 16 is moved relative to the outer sheath 42 of the release tool 14 toward the mitral valve so as to be exposed outside the outer sheath 42.

During the step for deploying each deployable element 54 of the pushing member 16, illustrated in FIG. 13, each lateral balloon 64 is inflated simultaneously.

The method next includes a step for pushing the first valve leaflet 18 face, illustrated in FIG. 14, during which the pushing member 16, and more specifically each lateral balloon 64, is moved along the central axis (Y) of the release tool 14 such that the outer pushing face 58 of each lateral balloon 64 comes into contact with the first face of the valve leaflet 18 and pushes the valve leaflet 18 to a withdrawn position, separated from the distal end 38 of the release tool 14.

The valve leaflet 18 is then kept in the withdrawn position by the pushing member 16 at least to the position of the proximal arms 32 on the first face of the leaflet 18.

The proximal arms 32 are then deployed and their second free ends are positioned on the first face of the leaflet 18 and/or on the mitral annulus 17, the proximal sleeve 26 still being covered by the outer sheath 42, as illustrated in FIG. 15.

Once the proximal arms 32 are positioned adequately, the central balloon 60 and each lateral balloon 64 are then deflated. The central balloon 60 is advanced outside the vicinity of the mitral valve in the left atrium 22A.

The method then comprises a step for radial pushing of the valve leaflets 18 in the trough 33A by the pushing member 16.

Each lateral balloon 64 is deflated again and deploys. During this deployment, the outer second faces of the lateral balloons 64 push the valve leaflets 18 into the troughs 33A of the proximal arms 32.

In a variant of the second embodiment, each deployable element 54 comprises a lateral rod 66. In FIG. 16, the pushing member 16 thus comprises two lateral rods 66 for two deployable elements 54.

Each lateral rod 66 extends between a proximal end connected to the inner rod 44 of the release tool 14 and a free end 68.

Each lateral rod 66 is deployable between a contracted configuration, not shown, in which the free end 68 of the lateral rod 66 is attached on the inner rod 44 of the release tool 14 such that the lateral rod 66 is substantially aligned with the central axis (Y), and a deployed configuration in which the lateral rod 66 is distally separated from the inner rod 44.

Each deployable element 54 includes a lateral balloon 64 positioned at the free end 68 of each lateral rod 66. Each lateral balloon 64 is inflatable independently of the configuration of the implant 12, and in particular independently of the configuration of the proximal sleeve 26.

Thus, each deployable element 54 is deployable radially relative to the central axis (Y) of the release tool 14 between a contracted state (not shown) corresponding to a state where the lateral balloon 64 is deflated and where the lateral rod 66 is in its contracted configuration, and a deployed state shown in FIG. 16, corresponding to a state where the associated lateral balloon 64 is inflated and where the lateral rod 66 is in its deployed configuration.

In the contracted state of each deployable element 54, i.e., when the associated lateral balloon 64 is deflated and when the lateral rod 66 is in its contracted configuration, the deployable element 54 is able to be kept in the hollow tubular external sheath 48 of the release tool 14. More specifically, each lateral rod 66 is able to go from its contracted configuration to its deployed configuration by moving the outer sheath 42 of the release tool 14 toward the proximal end of the release tool 14 to its intermediate configuration exposing the pushing member 16.

Furthermore, each deployable element 54 is, in its contracted state, movable relative to the proximal sleeve 26 along the central axis (Y) of the release tool 14, to be able to slide in the proximal sleeve 26 in the retracted or deployed configuration, so as to allow the withdrawal of the pushing member 16 before the installation of the implant 12, for example prior to the insertion of the distal tubular body of the distal sleeve 28 into the proximal tubular body 30A of the proximal sleeve 26.

A treatment method for a blood flow passage of an auricular-ventricular heart valve, using the treatment device 10 of this variant of the second embodiment, is similar to the treatment method for the second embodiment previously described, except that during the deployment step of each deployable element 54, each lateral rod 66 goes from its contracted configuration to its deployed configuration when the pushing member 16 is moved relative to the outer sheath 42 of the release tool 14 toward the mitral valve.

In another variant of the second embodiment, illustrated in FIG. 17, each lateral balloon 64 is inflatable independently of each other lateral balloon 64 and the central balloon 60. Thus, each lateral rod 66 is then connected by its proximal end to an auxiliary inner rod 70 independent of the inner rod 44 of the release tool 14.

In still another variant illustrated in FIG. 18, the pushing member 16 includes at least two deployable elements 54 each comprising a rib 72 deployable between a state close to the central axis (Y), not shown, when the pushing member 16 is arranged inside the tubular outer sheath 42, and a state distally separated from the central axis (Y) illustrated in FIG. 18, when the pushing member 16 is removed from the tubular outer sheath 42.

By moving the pushing member 16 outside the tubular outer sheath 42 of the release tool 14, each rib 72 is able to go from the close state to the distally separated state. In the example of FIG. 18, the pushing member 16 is removed from the tubular outer sheath 42 of the release tool 14.

Each deployable element 54 also includes a stay 74 connecting the inner rod 44 to the rib 72.

Each rib 72 comprises an outer pushing face 58 oriented perpendicular to or distally separated from the central axis (Y) of the release tool 14.

Each rib 72 advantageously comprises a second outer face intended to push the leaflets 18 radially in the troughs 33A of the proximal arms 32.

In one variant of the second embodiment, the pushing member 16 and the central balloon 60 form a single balloon. Such a balloon then includes a first central part, which, once inflated, corresponds in terms of function to the central balloon 60, and a second inflatable lateral part, which, once inflated, corresponds in terms of function to the pushing member 16.

Such a balloon is then inflatable in several configurations, in particular in a deflated configuration where the first central part and the lateral part are deflated, in a first inflated configuration where only the first central part is inflated, in a second inflated configuration where the first central part and the lateral part are inflated, and a third inflated configuration where only the lateral part is inflated.

Alternatively, the proximal arms 32 include, in the radially deployed configuration outside the release tool 14, at least one intermediate region having a substantially straight profile. The proximal arms 32 here are formed with a base of shape memory materials. The intermediate region is thus able to deform to arrange the receiving trough 33A of the leaflets 18.

In the treatment method, once the proximal arms 32 are positioned adequately on the valve leaflets 18 and/or on the mitral ring 17, the receiving trough 33A of the leaflets 18 forms owing to the shape memory, under the effect of the temperature. The leaflets 18 are next introduced into the troughs 33A, as previously described.

Owing to the pushing of the valve leaflets 18 into the withdrawn position by the pushing member 16, the device according to the invention makes it possible to ensure the correct positioning of the proximal arms 32 of the proximal sleeve 26, and therefore the proper installation of the implant 12.

The different forms of the pushing member 16 make it possible to slide between the chords of the sub-valvular mechanism and not to become tangled with the proximal arms 32 of the proximal sleeve 26.

The angle, with the central axis (X) of the implant 12, assumed by the proximal arms 32 makes it possible to provide additional gripping force for the leaflets 18, when the leaflets 18 are pinched between the proximal arms 32 and the distal arms 36.

Lastly, the concave trough 33A makes it possible to prevent contact between the valve leaflets 18 received in the troughs 33A and the proximal tubular body 30A of the proximal sleeve 26.

In one alternative, the proximal arms of the device do not necessarily comprise a receiving space for the valve leaflet delimited by the proximal arm, with no participation of the tubular armature.

The invention claimed is:

1. A treatment device for a biological valve, comprising:
an implant having a proximal sleeve, deployable between a retracted configuration and a deployed configuration, intended to be positioned in a blood flow passage delimited by the valve, the proximal sleeve comprising, at least in the deployed configuration, a proximal tubular body and a plurality of proximal arms, each extending between a first end connected to the tubular body, and a second free end intended to bear on a first face of a leaflet of the valve or on an annulus of the valve, and, in the deployed configuration, each free end is arranged radially away from the proximal tubular body,
a release tool for releasing the implant, extending longitudinally along a central axis between a proximal end and a distal end, the implant being mounted in the release tool in the retracted configuration,
wherein the device comprises a pushing member configured for pushing on the first face of the valve leaflet away from the free end of the proximal arms,
the pushing member being movable, in translation along the direction of the central axis relative to the implant kept in the retracted configuration in the release tool between a withdrawn position and a deployed position pushing the first face of the valve leaflet.

2. The treatment device according to claim 1, wherein the pushing member includes at least one deployable element, radially deployable relative to the central axis of the release tool between a contracted state and a deployed state, the deployment of the deployable element being independent of the deployment of the implant.

3. The treatment device according to claim 2, wherein the deployable element in the deployed state comprises an outer pushing face oriented perpendicular to or distally separated from the central axis of the release tool.

4. The treatment device according to claim 3, wherein the proximal arms are movable radially between a configuration contracted in the release tool and a configuration deployed radially outside the release tool, the deployable element in the deployed state being received between or in front of the proximal arms in the radially deployed configuration.

5. The treatment device according to claim 2, wherein the deployable element comprises at least one lateral balloon inflatable independently of the configuration of the implant.

6. The treatment device according to claim 5, wherein the pushing member comprises at least two lateral balloons distributed symmetrically on either side of the central axis of the release tool.

7. The treatment device according to claim 6, wherein the lateral balloons are able to be inflated independently or simultaneously.

8. The treatment device according to claim 2, wherein the pushing member includes a deformable hollow tubular external sheath extending up to a distal end and having longitudinal slits distributed circumferentially, two adjacent slits forming a pair, each pair of adjacent slits delimiting a deployable element, the pushing member including a rigid internal rod positioned inside the external sheath and connected to the distal end of the external sheath, the external sheath being movable along the central axis relative to the inner rod to deploy the deployable elements by moving the inner rod relative to the external sheath.

9. The treatment device according to claim 8, wherein the pushing member has a number of deployable elements greater than or equal to two.

10. The treatment device according to claim 1, including a central balloon extending along the central axis of the release tool.

11. The treatment device according to claim 1, wherein the pushing member includes an inner rod, with the same axis as the central axis of the release tool, inserted into the release tool, the deployable element being mounted at a distal end of the inner rod.

12. The treatment device according to claim 1, wherein the release tool includes a tubular outer sheath movable relative to the proximal sleeve between a covering position of the proximal arms and a release position of the proximal arms, the pushing member being movable independently of the sheath.

13. The device according to claim 1, wherein the implant comprises a distal sleeve deployable between a retracted configuration and a deployed configuration intended to be positioned in the blood flow passage, comprising a distal tubular body able to be inserted into the proximal tubular body of the proximal sleeve of the implant.

14. The device according to claim 13, wherein the distal sleeve includes a plurality of distal arms each extending between a first end connected to the distal tubular body and a second free end intended to press on a second face of a leaflet of the valve opposite the first face or on the annulus of the valve.

15. The device according to claim 1, wherein the proximal tubular body and the proximal arms form a single-piece assembly.

16. A method for treating a biological organ comprising a biological valve, the method comprising:
providing a treatment device according to claim 1,
inserting the release tool into the biological organ,
moving the pushing member in translation along the direction of the central axis, relative to the implant kept in the retracted configuration, the pushing member being moved to the deployed position,
pushing, by the pushing member, the first face of the valve leaflet with respect to the implant into a retracted position of the first face of the valve leaflet, and
keeping the first face of the tissue in the retracted position, while deploying the proximal arms of the implant, and moving the implant to arrange the proximal arms of the implant in contact with the first face of the valve.

17. The method according to claim 16, wherein the pushing member includes at least one deployable element, radially deployable relative to the central axis of the release tool between a contracted state and a deployed state, the deployment of the deployable element being independent of the deployment of the implant,
wherein, before pushing the first face of the valve leaflet, the method comprises deploying the deployable element of the pushing member into the deployed state, and the deployable element of the pushing member is used for pushing the first face, and
wherein, after the contact of the proximal arms of the implant with the first face of the valve, the method contracting the pushing member into the contracted state.

18. The method according to claim 16, wherein the pushing of the first face of the valve arranges a deployment area for the proximal arms of the implant.

19. The method according to claim 17, wherein each proximal arm protrudes away from the proximal tubular body and defines a receiving space for the valve leaflet delimited by the proximal arm, the receiving space being defined by the proximal arm between the connected end and the free end, and in an intermediate region of the proximal arm defining a trough for receiving the valve leaflet, and
wherein the method further comprises radial pushing of the valve leaflets in the trough via the pushing member, during which the deployable element is deployed in the deployed state, so that the deployable element pushes the valve leaflets into the troughs of the proximal arms.

20. The method according to claim 19, wherein the leaflets housed in the trough form a seal around the tubular armature.

* * * * *